(12) United States Patent
Gilman et al.

(10) Patent No.: US 10,143,851 B2
(45) Date of Patent: *Dec. 4, 2018

(54) ARRHYTHMIA ELECTROTHERAPY DEVICE AND METHOD WITH PROVISIONS FOR MITIGATING PATIENT DISCOMFORT

(71) Applicant: Galvani, Ltd., Eagan, MN (US)

(72) Inventors: Byron L. Gilman, Edina, MN (US); Mark W. Kroll, Crystal Bay, MN (US)

(73) Assignee: Galvani, Ltd., Eagan, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/496,075

(22) Filed: Apr. 25, 2017

(65) Prior Publication Data

US 2017/0291035 A1 Oct. 12, 2017

Related U.S. Application Data

(60) Continuation of application No. 14/922,792, filed on Oct. 26, 2015, now Pat. No. 9,636,504, which is a (Continued)

(51) Int. Cl.
 *A61N 1/00* (2006.01)
 *A61N 1/39* (2006.01)
 (Continued)

(52) U.S. Cl.
 CPC .......... *A61N 1/3962* (2013.01); *A61N 1/365* (2013.01); *A61N 1/3621* (2013.01);
 (Continued)

(58) Field of Classification Search
 CPC .... A61N 1/3702; A61N 1/3621; A61N 1/365; A61N 1/36542; A61N 1/3962; A61N 1/0563; A61N 1/0587; A61N 1/36132; A61N 1/36139; A61N 1/3956; A61N 1/39624
 See application file for complete search history.

(56) References Cited

U.S. PATENT DOCUMENTS 3,729,008 A 4/1973 Berkovits
3,738,370 A 6/1973 Charms
(Continued)

FOREIGN PATENT DOCUMENTS

EP 0314078 B1 10/1988
EP 0361517 A2 4/1990
(Continued)

OTHER PUBLICATIONS

US 5,584,866, 12/1996, Kroll et al. (withdrawn)
(Continued)

*Primary Examiner* — Scott Getzow
(74) *Attorney, Agent, or Firm* — Patterson Thuente Pedersen, P.A.

(57) ABSTRACT

Apparatus and method for treating an arrhythmia in a patient using an electrotherapy device such as a subcutaneous pacing device. The device applies a series of electrotherapy pulses in response to the presence of the arrhythmia. Various provisions are disclosed for mitigating pain or discomfort as a result of the electrotherapy pulses.

13 Claims, 9 Drawing Sheets

Related U.S. Application Data continuation of application No. 14/447,273, filed on Jul. 30, 2014, now Pat. No. 9,168,381, which is a division of application No. 14/103,841, filed on Dec. 11, 2013, now Pat. No. 8,868,178.

(60) Provisional application No. 61/735,832, filed on Dec. 11, 2012.

(51) Int. Cl.
    *A61N 1/365*     (2006.01)
    *A61N 1/362*     (2006.01)
    *A61N 1/37*     (2006.01)

(52) U.S. Cl.
    CPC ..... *A61N 1/36542* (2013.01); *A61N 1/36585* (2013.01); *A61N 1/3702* (2013.01)

(56) References Cited

U.S. PATENT DOCUMENTS

| | | |
|---|---|---|
| 3,942,536 A | 3/1976 | Mirowski et al. |
| 4,136,703 A | 1/1979 | Wittkampf |
| 4,375,817 A | 3/1983 | Engle et al. |
| 4,384,585 A | 5/1983 | Zipes |
| 4,727,877 A | 3/1988 | Kallok |
| 5,107,834 A | 4/1992 | Ideker et al. |
| 5,199,429 A | 4/1993 | Kroll et al. |
| 5,265,600 A | 11/1993 | Adams et al. |
| 5,275,621 A | 1/1994 | Mehra |
| 5,282,836 A | 2/1994 | Kreyenhagen et al. |
| 5,306,291 A | 4/1994 | Kroll et al. |
| 5,330,509 A | 7/1994 | Kroll et al. |
| 5,334,219 A | 8/1994 | Kroll |
| 5,365,391 A | 11/1994 | Sugiyama et al. |
| 5,372,605 A | 12/1994 | Adams et al. |
| 5,383,907 A | 1/1995 | Kroll |
| 5,387,613 A | 2/1995 | Goldberg et al. |
| 5,391,186 A | 2/1995 | Kroll et al. |
| 5,403,356 A | 4/1995 | Hill et al. |
| 5,405,363 A | 4/1995 | Kroll et al. |
| 5,407,444 A | 4/1995 | Kroll |
| 5,413,591 A | 5/1995 | Kroll |
| 5,433,729 A | 7/1995 | Adams et al. |
| 5,489,293 A | 2/1996 | Pless et al. |
| 5,545,182 A | 8/1996 | Stotts et al. |
| 5,545,204 A | 8/1996 | Cammilli et al. |
| 5,562,708 A | 10/1996 | Combs et al. |
| 5,620,464 A | 4/1997 | Kroll et al. |
| 5,620,468 A | 4/1997 | Mongeon et al. |
| 5,674,248 A | 10/1997 | Kroll et al. |
| 5,676,687 A | 10/1997 | Ayers |
| 5,683,429 A | 11/1997 | Mehra |
| 5,766,226 A | 6/1998 | Pedersen |
| 5,782,882 A | 7/1998 | Lerman |
| 5,792,187 A | 8/1998 | Adams |
| 5,797,967 A | 8/1998 | KenKnight |
| 5,800,465 A | 9/1998 | Thompson et al. |
| 5,813,999 A | 9/1998 | Ayers et al. |
| 5,840,079 A | 11/1998 | Warman et al. |
| 5,925,066 A | 7/1999 | Kroll et al. |
| 5,928,270 A | 7/1999 | Ramsey, III |
| 5,995,871 A | 11/1999 | Knisley |
| 5,999,852 A | 12/1999 | Elabbady et al. |
| 6,070,081 A | 5/2000 | Takahashi et al. |
| 6,081,746 A | 6/2000 | Pendekanti et al. |
| 6,085,116 A | 7/2000 | Pendekanti et al. |
| 6,085,119 A | 7/2000 | Scheiner et al. |
| 6,091,991 A | 7/2000 | Warren |
| 6,094,596 A | 7/2000 | Morgan |
| 6,141,588 A | 10/2000 | Cox et al. |
| 6,157,859 A | 12/2000 | Alt |
| 6,178,351 B1 | 1/2001 | Mower |
| 6,185,459 B1 | 2/2001 | Mehra et al. |
| 6,205,357 B1 | 3/2001 | Ideker et al. |
| 6,233,483 B1 | 5/2001 | Causey, III et al. |
| 6,246,906 B1 | 6/2001 | Hsu et al. |
| 6,292,691 B1 | 9/2001 | Pendekanti et al. |
| 6,327,500 B1 | 12/2001 | Cooper et al. |
| 6,463,330 B1 | 10/2002 | Rabinovitch et al. |
| 6,510,342 B1 | 1/2003 | Park et al. |
| 6,526,317 B2 | 2/2003 | Hsu et al. |
| 6,556,862 B2 | 4/2003 | Hsu et al. |
| 6,567,698 B2 | 5/2003 | Herleikson |
| 6,587,720 B2 | 7/2003 | Hsu et al. |
| 6,643,545 B2 | 11/2003 | Ideker et al. |
| 6,711,422 B2 | 3/2004 | Mawardi |
| 6,711,442 B1 | 3/2004 | Swerdlow et al. |
| 6,718,204 B2 | 4/2004 | Degroot et al. |
| 6,745,081 B1 | 6/2004 | Helland et al. |
| 6,754,525 B1 | 6/2004 | Province et al. |
| 6,763,266 B1 | 7/2004 | Kroll |
| 6,813,516 B2 | 11/2004 | Ujhelyi et al. |
| 6,832,982 B1 | 12/2004 | Lapanashvili et al. |
| 6,847,842 B1 | 1/2005 | Rodenhiser et al. |
| 6,937,896 B1 | 8/2005 | Kroll |
| 7,006,867 B1 | 2/2006 | Kroll |
| 7,020,517 B2 | 3/2006 | Weiner |
| 7,047,071 B2 | 5/2006 | Wagner et al. |
| 7,079,891 B1 | 7/2006 | Kroll |
| 7,110,811 B2 | 9/2006 | Wagner et al. |
| 7,113,822 B1 | 9/2006 | Kroll |
| 7,120,490 B2 | 10/2006 | Chen et al. |
| 7,127,292 B2 | 10/2006 | Warman et al. |
| 7,139,611 B1 | 11/2006 | Kroll et al. |
| 7,142,927 B2 | 11/2006 | Benser et al. |
| 7,142,928 B2 | 11/2006 | Sharma et al. |
| 7,155,286 B1 | 12/2006 | Kroll et al. |
| 7,164,944 B1 | 1/2007 | Kroll et al. |
| 7,181,276 B1 | 2/2007 | Province et al. |
| 7,231,255 B1 | 6/2007 | Kroll et al. |
| 7,277,755 B1 | 10/2007 | Falkenberg et al. |
| 7,386,342 B1 | 6/2008 | Falkenberg et al. |
| 7,480,351 B2 | 1/2009 | Hiatt, Jr. et al. |
| 7,509,170 B2 | 3/2009 | Zhang et al. |
| 7,532,933 B2 | 5/2009 | Hastings et al. |
| 7,556,631 B2 | 7/2009 | Hieshima et al. |
| 7,647,109 B2 | 1/2010 | Hastings et al. |
| 7,738,954 B1 | 6/2010 | Kroll et al. |
| 7,751,887 B1 | 7/2010 | Kroll et al. |
| 7,848,823 B2 | 12/2010 | Drasler et al. |
| 7,899,537 B1 | 3/2011 | Kroll et al. |
| 7,925,343 B1 | 4/2011 | Min et al. |
| 8,032,218 B2 | 10/2011 | Wong et al. |
| 8,121,680 B2 | 2/2012 | Falkenberg et al. |
| 8,175,702 B2 | 5/2012 | Efimov et al. |
| 8,204,605 B2 | 6/2012 | Hastings et al. |
| 8,306,619 B2 | 11/2012 | Krig et al. |
| 8,423,134 B2 | 4/2013 | Buschman et al. |
| 8,473,305 B2 | 6/2013 | Belcher et al. |
| 8,509,889 B2 | 8/2013 | Efimov et al. |
| 8,532,793 B2 | 9/2013 | Morris et al. |
| 8,548,585 B2 | 10/2013 | Ternes et al. |
| 8,868,178 B2 | 10/2014 | Gilman et al. |
| 9,168,381 B2 | 10/2015 | Gilman et al. |
| 9,636,504 B2 | 5/2017 | Gilman et al. |
| 2001/0014816 A1 | 8/2001 | Hsu et al. |
| 2002/0035382 A1* | 3/2002 | Rubin ................. A61N 1/3906 607/5 |
| 2002/0082658 A1* | 6/2002 | Heinrich .............. A61N 1/3622 607/9 |
| 2002/0128565 A1 | 9/2002 | Rudy |
| 2003/0083727 A1 | 5/2003 | Casavant et al. |
| 2003/0120316 A1 | 6/2003 | Spinelli et al. |
| 2003/0220676 A1 | 11/2003 | Helland |
| 2004/0111123 A1 | 6/2004 | Ware et al. |
| 2004/0210256 A1 | 10/2004 | Musley et al. |
| 2004/0215258 A1 | 10/2004 | Lovett et al. |
| 2005/0096701 A1 | 5/2005 | Donovan et al. |
| 2005/0154420 A1 | 7/2005 | Diaz et al. |
| 2005/0197676 A1 | 9/2005 | Kroll et al. |
| 2006/0161206 A1 | 7/2006 | Efimov et al. |
| 2007/0021793 A1 | 1/2007 | Voegele et al. |
| 2007/0088395 A1 | 4/2007 | Province et al. |

(56) References Cited

U.S. PATENT DOCUMENTS

| | | | |
|---|---|---|---|
| 2007/0135847 A1 | 6/2007 | Kenknight | |
| 2008/0039904 A1 | 2/2008 | Bulkes et al. | |
| 2008/0234769 A1 | 9/2008 | Falkenberg et al. | |
| 2009/0062877 A1 | 3/2009 | Krinski et al. | |
| 2009/0204164 A1 | 8/2009 | Efimov et al. | |
| 2010/0016917 A1 | 1/2010 | Efimov et al. | |
| 2010/0249860 A1* | 9/2010 | Shuros | A61N 1/3625 607/4 |
| 2011/0009916 A1 | 1/2011 | Efimov et al. | |
| 2011/0029032 A1 | 2/2011 | Bardy et al. | |
| 2012/0203297 A1 | 8/2012 | Efimov et al. | |
| 2012/0209343 A1 | 8/2012 | Efimov et al. | |
| 2013/0282073 A1 | 10/2013 | Cowan et al. | |
| 2013/0289646 A1 | 10/2013 | Libbus et al. | |
| 2014/0180351 A1 | 6/2014 | Gilman et al. | |
| 2015/0032170 A1 | 1/2015 | Gilman et al. | |
| 2016/0206885 A1 | 7/2016 | Gilman et al. | |

FOREIGN PATENT DOCUMENTS

| | | |
|---|---|---|
| EP | 0393265 A1 | 10/1990 |
| EP | 0833680 B1 | 3/1997 |
| EP | 1062971 A1 | 12/2000 |
| GB | 2025236 A | 1/1980 |
| WO | WO 1996/011035 A1 | 4/1996 |
| WO | WO 1999/051300 A2 | 10/1999 |
| WO | WO 2006/042295 A1 | 4/2006 |
| WO | WO 2008/063498 A1 | 5/2008 |
| WO | WO 2011/163339 A1 | 12/2011 |

OTHER PUBLICATIONS

A. Sambelashvili et al., "Nonlinear effects in subthreshold virtual electrode polarization," Am. J. Physiol. Heart Circ, Physiol., 2003, 284(6):H2368-H2374.
Allessie et al., "Regional Control of Atrial Fibrillation by Rapid Pacing in Conscious Dogs", Circulation, vol. 84, No. 4, Oct. 1991, pp. 1689-1697, USA.
Babbs et al., "Therapeutic indices for transchest defibrillator shocks: Effective, damaging, and lethal electrical doses," Am. Heart J., vol. 99, No. 6, pp. 734-738, Jun. 1980.
C. Larson et al., "Analysis of Electrically-Induced Reentrant Circuits in a Sheet of Myocardium," Annals Biomed. Eng., 2003, 31:768-780.
C. Ramanathan, "Noninvasive electrocardiographic imaging for cardiac electrophysiology and arrhythmia," Nature Medicine, Apr. 2004, 10(4):422-428.
Cartee et al., "The Transient Subthreshold Response of Spherical and Cylindrical Cell Models to Extracellular Stimulation", IEEE Trans. Biomed. Eng., vol. 39, No. 1, Jan. 1992, pp. 76-85.
Cheng et al., "Virtual Electrode-Induced Reexcitation: A Mechanism of Defibrillation," Circulation Research, 1999, 85(11):1056-66, USA.
Cherry et al, "Visualization of spiral and scroll waves in simulated and experimental cardiac tissue", New J. Phys., vol. 10, pp. 125016-125059, 2008.
Daoud et al., "Response of Type I Atrial Fibrillation to Atrial Pacing in Humans", Circulation, vol. 94, No. 5, 1996, 13 pages, USA.
Davidenko et al., "Stationary and drifting spiral waves of excitation in isolated cardiac muscle," Nature, vol. 355, pp. 349-351, Jan. 23, 1992.
Disertori et al., "Antitachycardia pacing therapies to terminate atrial tachyarrhythmias: the AT500 Italian Registry", European Heart Journal Supplements, 2001, pp. 16-24, USA.
Efimov et al., "Fast Fluorescent Mapping of Electrical Activity in the Heart: Practical Guide to Experimental Design and Applications", Chapter 7, pp. 131-156, 2003.
Efimov et al., "Transmembrane Voltage Changes Produced by Real and Virtual Electrodes During Monophasic Defibrillation Shock Delivered by an Implantable Electrode," Journal of Cardiovascular Electrophysiolgy, 1997, 8(9):1031-45, USA.
Efimov et al., "Virtual Electrode-Induced Phase Singularity: A Basic Mechanism of Difbrillation Failure," Circulation Research, 1998, 82(8):918-25, USA.
F. Aguel et al., "Advances in Modeling Cardiac Defibrillation," Int'l Journal of Bifurcation & Chaos, 2003, 13(12):3791-3803.
F. Qu et al., "Mechanisms of Superiority of Ascending Ramp Waveforms: New Insights into Mechanisms of Shock-induced Vulnerability and Defibrillation," Am. J. Physiol. Heart Circ. Physiol., 2005, 289:H569-H577.
F. Qu et al., "The Gurvich waveform has lower defibrillation threshold than the Zoll waveform and the truncated exponential waveform in the rabbit heart," Can. J. Physiol. Pharmacol., 2005, 83:152-160.
Fast et al., "Activation of Cardiac Tissue by Extracellular Electrical Shocks: Formation of 'Secondary Sources' at Intercellular Clefts in Monolayers of Cultured Myocytes," Circ. Res., vol. 82, pp. 375-385, 1998.
Fenton et al., "Multiple mechanisms of spiral wave breakup in a model of cardiac electrical activity," Chaos, vol. 12, No. 3, pp. 852-892, Sep. 2002.
Fenton et al., "Termination of Atrial Fibrillation Using Pulsed Low-Energy Far-Field Stimulation," Circulation, vol. 120, pp. 467-476, 2009.
Fenton et al., "Vortex dynamics in three-dimensional continuous myocardium with fiber rotation: Filament instability and fibrillation," Chaos, vol. 8, No. 1, pp. 20-47, Mar. 1998.
Fishler et al., "Spatiotemporal Effects of Syncytial Heterogeneities on Cardiac Far-field Excitations during Monophasic and Biphasic Shocks", Journal of Cardiovascular electrophysiolgy, 1998, 9(12):1310-24, USA.
Fishler, "Syncytial Heterogeneity as a Mechanism Underlying Cardiac Far-Field Stimulation During Defibrillation-Level Shocks," Journal of Cardiovascular Electrophysiolgy, 1998, 9(4):384-94, USA.
Gray et al, "Termination of spiral waves during cardiac fibrillation via shock-induced phase resetting," Proc. Natl. Acad. Sci. USA, vol. 102, No. 13, pp. 4672-4677, Mar. 29, 2005.
Gray et al., "Several small shocks beat one big one", Nature, vol. 475, Jul. 14, 2011, pp. 181-182.
Gray et al., "Spatial and temporal organization during cardiac fibrillation," Nature, vol. 392, pp. 75-78, May 14, 1998.
Grosu et al., "Learning and Detecting Emergent Behavior in Networks of Cardiac Myocytes", Communications of the ACM, Mar. 2009, pp. 97-104, vol. 52, No. 3.
H. G. Li et al., "Defibrillation Shocks Produce Different Effects on Prukinje Fibers and Ventricular Muscle: Implications for Successful Defibrillation, Refibrillation and Postshock Arrhythmia", J Am Coll Cardiol, 1993, 22:607-614.
Hooks et al, "Cardiac Microstructure: Implications for Electrical Propagation and Defibrillation in the Heart," Circ. Res., vol. 91, pp. 331-338, 2002.
Hucker et al., "Atrioventricular conduction with and without AV nodal delay: two pathways to the bundle of His in the rabbit heart", Am J. Physiol. Heart Circ. Physiol., 2007, 293:H1122-H1130, USA.
I. Kodama et al., "Aftereffects of high-intensity DC stimulation of the electromechanical performance of ventricular muscle", Am J. Physiol., 1994, 267:H248-H258.
I. R. Efimov et al., "Diastolic Shocking Experience: Do Virtual Anodes Exist Only During Systole?", J. Cardiovascular Electrophysiology, Nov. 2003, 14(11):1223-1224.
I. R. Efimov, "Fibrillatin or Neurillation: Back to the future in our concepts of sudden cardiac death?", Circ. Res., May 30, 2003, 92(10):1062-1064.
Ideker et al., "Correlation Among Fibrillation, Defibrillation and Cardiac Pacing", Pacing Clin. Electrophysiol., vol. 18, Mar. 1995, pp. 512-525.
J. T. Niemann et al., "Intracardiac Voltage Gradients during Transthoracic Defibrillation: Implications for Postshock Myocardial Injury," Acad. Emerg. Med., Feb. 2005, 12(2):99-105.

(56) References Cited

OTHER PUBLICATIONS

Joung et al., "Intracellular Calcium and the Mechanism of Anodal Supernormal Excitability in Langendorff Perfused Rabbit Ventricles," National Institutes of Health. Circ J. 2011; 75(4):834-843.
Kassab, "Scaling laws of vascular trees: of form and function," Am. J. Physiol. Heart Circ. Physiol., vol. 290, pp. H894-H903, 2006.
Kirchof et al, "Regional entrainment of Atrial Fibrillation Studied by High-Resolution Mapping in Open-Chest Dogs," Circulation, vol. 88, pp. 736-749, 1993.
Koster et al., "A randomized trial comparing monophasic and biphasic waveform shocks for external cardioversion of atrial fibrillation," Am. Heart. J. vol. 147, pp. e1-e7, 2004.
L. Li et al., "Effects of Lidocaine on Shock-Induced Vulnerability", J. Cardiovascular Electrophysiology, Oct. 2003, 14(10):S237-S248.
L. Li et al., "Mechanisms of enhance shock-induced arrhytmogenesis in the rabbit heart with healled myocardial infaraction," Am. J. Physiol. Heart Circ. Physiol., May 3, 2005, 289:H1054-H1068.
Ladwig et al., "Absence of an Impact of Emotional Distress on the Perception of Intracardiac Shock Discharges," International Journal of Behavioral Medicine, 2003, 10(1):56-65, USA.
M. Hillebrenner et al., "Postshock arrhythmogenesis in a slice of the canine heart," J. Cardiovasc. Electrophys., 2003, 14:S249-S256.
Mackenzie, "Making sense of a heart gone wild," Science, vol. 303, pp. 786-787, Feb. 6, 2004.
Maleckar et al., "Polarity reversal lowers activation time during diastolic field stimulation of the rabbit ventricles: insights into mechanisms," Am. J. Physiol. Heart Circ. Physiol., vol. 295, pp. H1626-1633, 2008.
Mowrey et al., "Membrane Time Constant During Internal Defibrillation Strength Shocks in Intact Heart: Effects of Na.Sup.+ and Ca.sup2+ Channel Blockers," J. Cardiovascular Electrophysiology, Apr. 25, 2004, Jun. 8, 2008, and Jan. 2009, 20(1):85-92, USA.
Murray, "The Physilogical Prnciple of Minimum Work: I. The Vascular System and the Cost of Blood Volume," Proc. Natl. Acad. Sci. USA, vol. 12, pp. 207-214, 1926.
N. S. Peters et al., "Disturbed Connexin43 Gap Junction Distribution Correlates With the Location of Reentrant Circuits in the Epicardial Border Zone of Healing Canine Infarcts That Cause Ventricular Tachycardia," Circulation, 1997, 95:988-996.
N. Trayanova et al., "Virtual Electrode-Induced Positive and Negative Graded Responses: New Insights into Fibrillation Induction and Defibrillation," J. Cardiovascular Electrophysicology, 2003, 14(7):756-763.
Plonsey, "The Nature of Sources of Bioelectric and Biomagnetic Fields," Biophys. J., vol. 39, pp. 309-312, 1982.
Pumir et al, "Wave Emission from Heterogeneities Opens a Way to Cotnrolling Chaos in the Heart," Phys. Rev. Lett., vol. 99, pp. 208101-1, 2007.
Pumir et al., "Unpinning of a Rotating Wave in Cardiac Muscle by an Electric Field", J. Theor. Biol., vol. 199, 1999, pp. 311-319, USA.
Rappel et al, "Spatiotemporal Control of Wave Instabilities in Cardiac Tissue," Phys. Rev. Lett., vol. 83, No. 2, pp. 456-459, Jul. 12, 1999.
Ripplinger et al., "Mechanisms of unpinning and termination of ventricular tachycardia", Am J. Physiol. Heart Circ. Physiol., 2006, pp. H184-H192.
Roth et al., "A Bidomain Model for the Extracellular Potential and Magnetic Field of Cardiac Tissue," IEEE Trans. Biomed. Eng., vol. 33, No. 4, pp. 467-469, Apr. 1986.
S. Takagi et al., "Unpinning and Removal of a Rotating Wave in Cardiac Muscle", Phys. Review Letters, Jul. 30, 2004, 93(5):058101-1-058101-4.
Sakurai et al., "Design and Control of Wave Propagation Patterns in Excitable Media," Science, vol. 296, pp. 2009-2012, Jun. 14, 2002.
Sambelashvili et al., "Virtual electrode theory explains pacing threshold increase caused by cardiac tissue damage," Am. J. Physiol. Heart Circ. Physiol., vol. 286, pp. H2183-H2194, 2004.
Santini et al., "Single Shock Endocavitary Low Energy Intracardiac Cardioversion of Chronic Atrial Fibrillation," J. Interv. Card. Electrophysiol., vol. 3, pp. 45-51, 1999.
Sepulveda et al., "Current injection into a two-dimensional anisotropic bidomain", Biophys. J., vol. 55, May 1989, pp. 987-999, USA.
Sobie et al., "A Generalized Activating Function for Predicting Virtual Electrodes in Cardiac Tissue", Biophys. J., vol. 73, Sep. 1997, pp. 1410-1423.
T. Ashihara et al., "Spiral Wave Control by a Localized Stimulus: A Bidomain Model Study," J. Cardiovascular Electrophysiology, Feb. 2004 15(2):226-233.
Trayanova et al., "Modeling Defibrillation: Effects of Fiber Curvature," J. Electrocardiol., vol. 31 (suppl.), pp. 23-29, 1998.
Trayanova et al., "The Response of a Spherical Heart to a Uniform Electric Field: A Bidomain Analysis of Cardiac Stimulation", J. IEEE trans. Biomed. Eng., vol. 40, No. 9, Sep. 1993, pp. 899-908.
Tsukerman et al., "Defibrillation of the Heart by a Rotating Current Field," Kardiologiia, 1973, 13(12):75-80, USA.
V. Nikolski et al., "Fluorescent Imaging of a Dual-Pathway Atrio-ventricular-Nodal Conduction System," Circ Res., Feb. 16, 2001, pp. 1-7.
Walcott et al., "Do clinically relevant transthoracic defibrillation energies cause myocardial damage and dysfunction?" Resuscitation, vol. 59, pp. 59-70, 2003.
Witkowski et al, "Spatiotemporal evolution of ventricular fibrillation," Nature, vol. 392, pp. 78-82, Mar. 5, 1998.
X. Zhou et al., "Epicardial Mapping of Ventricular Defibrillation with Monophasic and Biphasic Shocks in Dogs," Circulation Research, Jan. 1993, 72(1):145-160.
Y. Cheng et al., "Mechanisms of Shock-Induced Arrhythmogenesis During Acute Global Ischemia", Am J Physiol. Heart Circ. Physiol., Jun. 2002, 282(6):H2141-51.
Y. Cheng et al., "Shock-induced arrhythmogenesis is enhance by 2,3-butanedione monoxime compared with cytochalasin D," Am. J. Physiol. Heart Circ. Physiol., 2004, 286:H310-H318.
Zheng et al., "Reduction of the Internal Atrial Defibrillation Threshold with Balanced Orthogonal Sequential Shocks," Journal of Cardiovascular Electrophysiolgy, 2002; 13(9):904-9, USA.
EP13862671.8 Supplementary European Search Report dated Sep. 6, 2016, 6 pages.
EP13862671.8 Supplementary European Search Report dated Jan. 4, 2017, 11 pages.
Written Opinion and International Search Report for International Application No. PCT/IB2013/002917, dated May 1, 2014, 17 pages.
Application and File History for U.S. Appl. No. 14/103,841, filed Dec. 11, 2013, now U.S. Pat. No. 8,868,178. Inventors: Gilman et al.
Application and File History for U.S Appl. No. 14/447,273, filed Jul. 30, 2014, now U.S. Pat. No. 9,168,381. Inventors: Gilman et al.
Application and File History for U.S. Appl. No. 14/922,792, filed Oct. 26, 2015. Inventors: Gilman et al.
Application and File History for U.S. Appl. No. 12/33,257, filed Dec. 11, 2008, now U.S. Pat. No. 8,509,889. Inventors: Efimov et al.

* cited by examiner

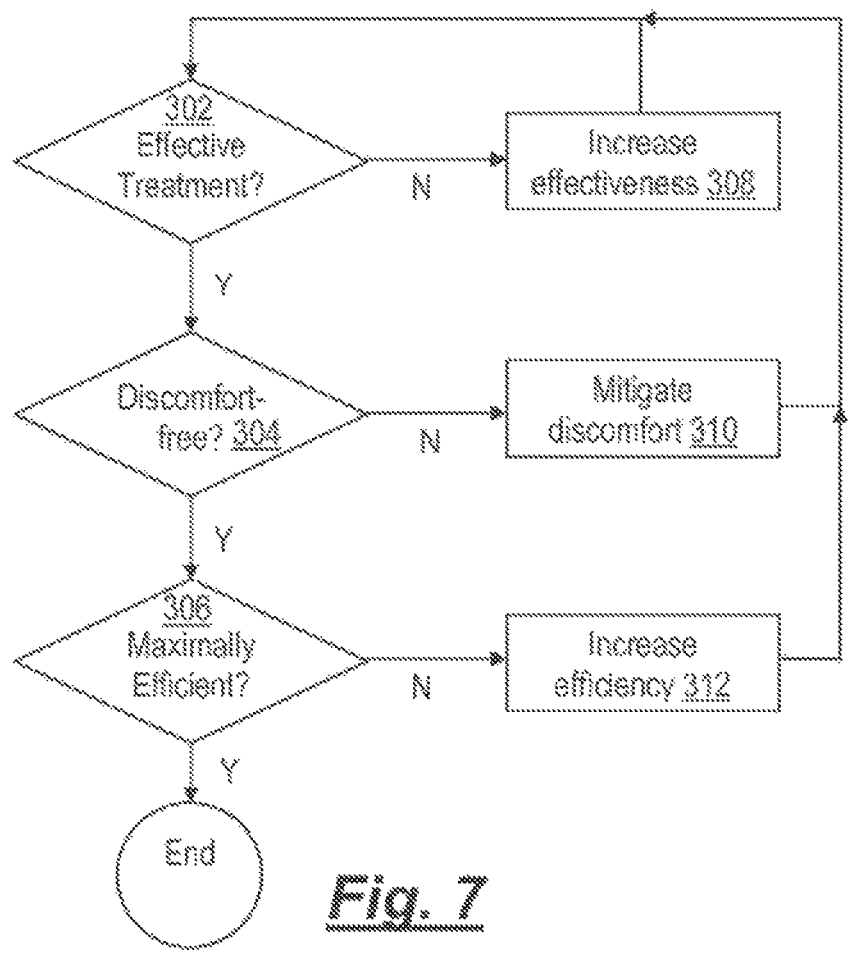

ARRHYTHMIA ELECTROTHERAPY DEVICE AND METHOD WITH PROVISIONS FOR MITIGATING PATIENT DISCOMFORT

RELATED APPLICATIONS

This application is a continuation of U.S. application Ser. No. 14/922,792, filed Oct. 26, 2015, now issued as U.S. Pat. No, 9,636,504, which in turn is a continuation of U.S. application Ser. No. 14/447,273, filed Jul. 30, 2014, now issued as U.S. Pat. No. 9,168,381, which in turn is a division of U.S. application Ser. No. 14/103,841, filed Dec. 11, 2013, now issued as U.S. Pat. No. 8,868,178, which claims the benefit of U.S. Provisional Application No. 61/735,832, filed Dec. 11, 2012, each of which is hereby fully incorporated herein by reference.

FIELD OF THE INVENTION

This disclosure relates generally to the field of electrotherapy apparatus and associated methods and, more particularly, to the treatment of arrhythmias using artificial pacing pulses produced by an implantable subcutaneous device that are capable of causing discomfort in the patient as an undesired side-effect of the treatment.

BACKGROUND OF THE INVENTION

Cardiac arrest is a significant public health problem cutting across age, race, and gender. A positive impact on cardiac arrest survival has been demonstrated with the substantial reduction in time to defibrillation (the administration of a high energy electrical shock to the heart) provided by the widespread deployment of automated external defibrillators and the use of implantable cardioverter defibrillators (ICDs). Defibrillators have had a major impact on dealing with cardiac arrest in that they are the only reliable treatment for ventricular fibrillation (VF.)

Defibrillators can be implanted or external and can include additional capabilities of cardioversion, bradycardia pacing (brady pacing) and anti-tachycardia pacing (anti-tachy pacing or ATP). A recent development in implantable defibrillators is to design the pulse generator and electrodes to be suitable for subcutaneous implantation, thus avoiding the need for an intracardiac electrode. This method has the advantage of potentially simpler surgical procedures and not requiring fluoroscopic facilities to position an intracardiac electrode. Although less invasive than intra-cardiac electrodes, devices utilizing subcutaneous electrodes must apply relatively higher-amplitude pulses to achieve a comparable therapeutic effect as devices employing intra-cardiac electrodes. This requirement is attributable primarily to the greater distance between the subcutaneous electrodes and the resulting wider, less-focused dispersal of charge into the body, making cardiac cell capture less efficient.

In addition to defibrillation, which is often delivered when the patient is unconscious, modern defibrillators also deliver brady pacing, ATP, and cardioversion therapies. In these therapies, the patient is usually conscious and the discomfort associated with subcutaneous delivery of these therapies (particularly ATP and cardioversion) has prevented their use in subcutaneous devices. A solution is needed to mitigate the discomfort associated with these treatments using subcutaneous implantable pulse generators and electrodes.

SUMMARY OF THE INVENTION

One aspect of the present invention is directed to treating an arrhythmia in a patient using an electrotherapy device. The treatable arrhythmia can be a tachycardia or bradycardia. The implantable device can be a subcutaneous pulse generator with subcutaneous electrodes that apply far-field pacing pulses.

In a related aspect of the invention, an electrotherapy device includes a power source adapted to supply energy for operation of the apparatus, electrotherapy administration circuitry electrically coupled to the power source and to a set of patient terminals, and constructed to generate electrotherapy pulses using the energy from the power source and apply a series of the electrotherapy pulses via the patient terminals in response to a control signal, the electrotherapy pulses being far-field pacing pulses, each delivering sufficient charge, through a set of electrodes positioned subcutaneously in far-field fashion relative to a heart of the patient, to initiate a cardiac cycle, and monitoring circuitry electrically coupled with the power source and the set of patient terminals, and constructed to monitor the patient for indicia of the arrhythmia.

Also included is controller circuitry electrically coupled with the power source, the electrotherapy administration circuitry, and the monitoring circuitry, the controller circuitry including a processor and a data storage device containing instructions that, when executed by the processor, cause the controller circuitry to read an output of the monitoring circuitry and determine any presence of the arrhythmia based on that output, and to generate the control signal causing the electrotherapy administration circuitry to apply the series of electrotherapy pulses.

The electrotherapy device monitors the patient for indicia of the arrhythmia, determines the presence of the arrhythmia based on the indicia, and applies a series of electrotherapy pulses in response to the presence of the arrhythmia as a result of the determining, each of the pulses of the series having a rising edge, a peak amplitude, and a trailing edge.

In one embodiment, the electrotherapy device applies a first slew rate for a first portion of each rising edge of each pulse of the series of electrotherapy pulses, and a second slew rate for a second portion of each rising edge of each pulse of the series of electrotherapy pulses.

In another embodiment, the electrotherapy administration circuitry includes a pulse shaping circuit constructed such that, in operation, the pulse shaping circuit applies a half-wave sinusoidal pulse wave shape for at least a major part of a duration of each pulse, the sinusoidal pulse wave shape including a rising portion and a falling portion.

In another embodiment, the controller circuitry stores a plurality of approved electrotherapy application vectors, each one of which is associated with a corresponding set of electrotherapy pulse parameters including a minimum peak pulse amplitude limit established during in-situ testing in the patient, and executes a parameter setting input module utilizing communication circuitry to accept configuration instructions to vary the electrotherapy application vector.

In another embodiment, the device includes evoked response sensing circuitry electrically coupled to the controller circuitry, the evoked response sensing circuitry being constructed to sense indicia of movement by the patient, and the controller circuitry being further configured to infer whether the movement is an evoked response to the administration of the electrotherapy pulses, and to adjust application of subsequent electrotherapy pulses in response to an inference of the evoked discomfort response.

BRIEF DESCRIPTION OF THE DRAWINGS

The invention may be more completely understood in consideration of the following detailed description of various embodiments of the invention in connection with the accompanying drawings, in which:

FIG. 7 is a flow diagram illustrating steps to automate optimization of electrotherapy administration such as far-field pacing by a subcutaneous device according to one embodiment.

Figure 1:
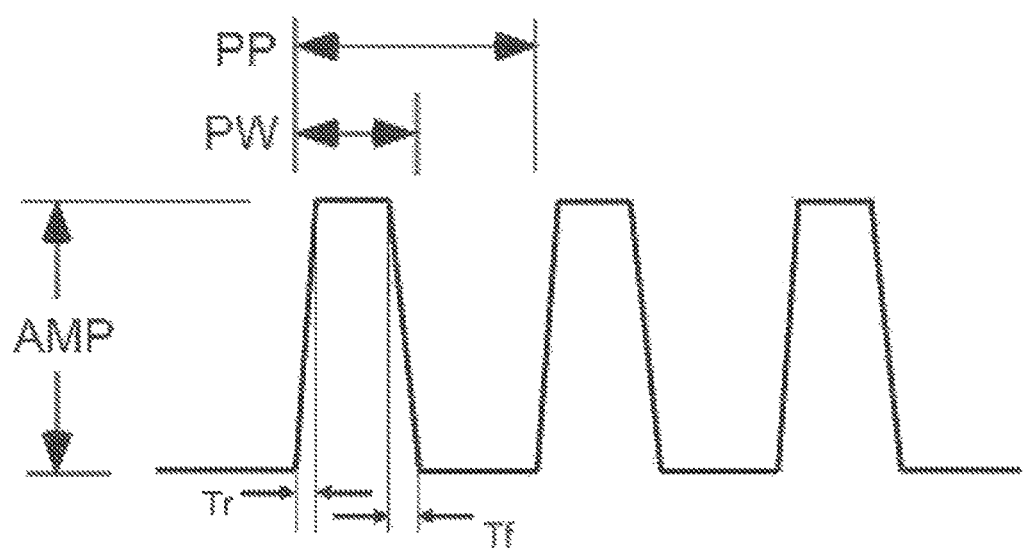
FIG. 1 is a waveform diagram illustrating various conventional pacing parameters, certain values of which can be used to mitigate discomfort associated with electrotherapy according to aspects of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

This disclosure addresses methods of reducing the discomfort of ATP and cardioversion and enabling them to be clinically useful in subcutaneous defibrillators as well as traditional ICDs. The basic concepts of ATP and cardioversion are known and have been described in U.S. Pat. Nos. 6,718,204 and 4,375,817, the disclosures of which are incorporated by reference herein, except for any express definitions stated therein insofar as they are inconsistent with the terminology of the present disclosure.

One aspect of the invention is directed to delivering effective electrotherapy for treating cardiac arrhythmias while mitigating the discomfort experienced by the patient as a result of the treatment. Patient discomfort in the present context includes pain or, more generally, an unpleasant sensation, along with the largely psychological discomfort from an involuntary muscle flinch due to motor neuron stimulation as a byproduct of the cardiac stimulation.

One type of application for this aspect of the invention is in far-field anti-tachycardia pacing (ATP) (e.g., as implemented with a subcutaneous implanted device), where the pacing pulse has a large enough amplitude to be felt by the patient. Other applications can include far-field electrostimulation of the heart where pulse amplitudes are in the range of 30 mA-80 mA.

According to one embodiment, discomfort of the patient is mitigated by applying pacing pulses targeting the heart with a reduced spectral power in the higher frequencies compared with conventional pulses applied by present-day implantable pulse generators. For instance, the pulses according to this embodiment and have slower rise and fall times (i.e., a slower slew rate). This approach recognizes the fact that sharp pain receptors (e.g., thinly myelinated type III (A-delta) fibers) have time constants generally in the range of 100-600 µs, whereas the effective time constant associated with myocardial cells is in the range of 1-5 ms—notably, an order of magnitude slower than the time constant associated with the pain receptors. According to one particular embodiment, the electrotherapy pulses are 3-15 ms in duration. In a related embodiment, the pulses have a duration in the range of 4-8 ms. In a specific case, a particular pulse duration of 5 ms is employed.

For pulse durations in this range, cardiac capture is largely a function of the delivered charge in the pulse. Although the actual charge required for cardiac capture increases with duration, this increases at a much slower rate than it does for nerve stimulation since the cardiac cell chronaxie is greater. Thus, in a related embodiment, the pulse waveform characteristic is such that a sufficient charge is delivered to achieve reliable cardiac capture, while the amplitude profile is such that sharp peaks are avoided. By reducing the peak amplitude relative to conventional waveforms used with subcutaneous treatments, this waveform can reduce the patient's discomfort, and by lengthening the pulse width the equivalent total charge is delivered as with higher-peak waveforms. This approach accepts a modest trade-off in stimulation efficacy and energy efficiency compared with conventional waveforms.

A generalized depiction of an electrotherapy pacing waveform is shown in FIG. 1. The general waveform is composed of a plurality of pulses that are timed to coincide with the heart rate to be controlled. The pulse period PP is the inverse of this rate. The individual pulses, from start to finish, have a defined pulse width PW. For each pulse, there is a rising edge having a rise time Tr, and a falling, or trailing, edge having a fall time Tf as shown. Each pulse has a peak amplitude labeled AMP.

As an illustrative example, for anti-tachycardia pacing and anti-bradycardia pacing, Table 1 below provides an exemplary range of parameter values corresponding to empirically determined effectiveness.

TABLE 1

Exemplary Parameter Value Ranges for Implanted PacingDevices

| Parameter | Value of Parameter ATP Device | Value of Parameter Antibradicardia Device |
| --- | --- | --- |
| Pulse Rate | 150-250 per min. | 50-100 per min. |
| Pulse Current Amplitude | 30-80 mA | 15-75 mA |
| Pulse Width | 3-15 ms | 3-15 ms |
| Pulse Period | 240-400 ms | 600-1200 ms |
| Rise time | 0.05-4 ms | 0.05-4 ms |
| Fall time | 0.05-4 ms | 0.05-4 ms |

The wave shape of each pulse is defined by these parameters, along with other parameters that establish the time-varying characteristic of each part of the pulse. For instance, in the simple example depicted in FIG. 1, we have trapezoidal pulse waveforms in which the rising and falling edges are linear, and where the peak amplitude is maintained at a steady level for a significant portion of each pulse's duration.

Figure 2A:
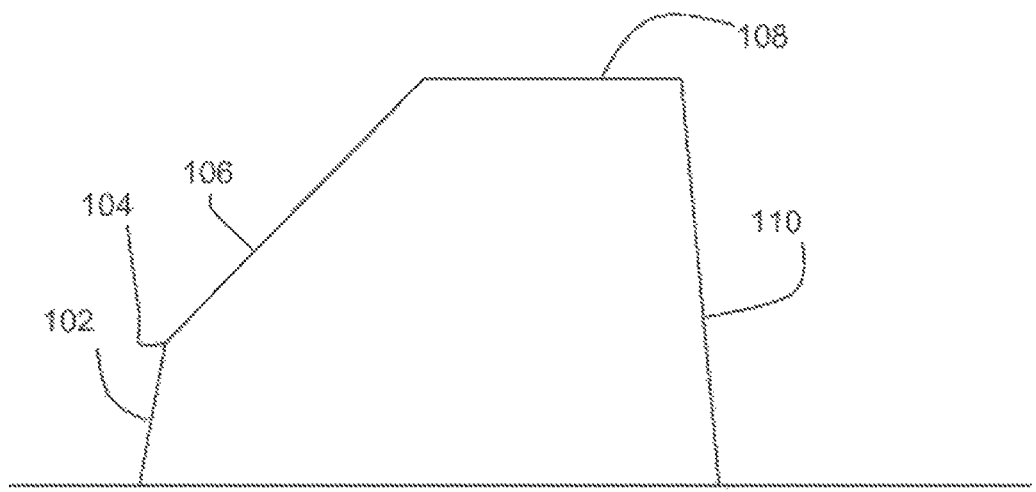
FIGS. 2A-2D are various waveform diagrams illustrating electrotherapy pulses having characteristics beneficial for discomfort mitigation according to aspects of the invention.

The pacing waveform can be varied according to other embodiments by applying waveshaping techniques. FIG. 2A illustrates a waveform for a single pulse produced by one such approach. In this example, the waveshaping technique being applied is a variable slew rate limiting. This pulse begins with an initially fast rise time 102 until a point 104 where the slew rate is slowed to a more gradual rising edge 106. The peak amplitude 108 is maintained for a predetermined duration (e.g., on the order or milliseconds), after which time the pulse is truncated with a relatively fast falling edge 110.

In general, the effectiveness of a pacing pulse is correlated to the total charge (i.e., in coulombs) delivered across the duration of the pulse width. In a traditional pacing pulse, a higher pulse amplitude and shorter pulse duration could be used to deliver an effective charge sufficient to capture enough cells in the heart to initiate a heartbeat most efficiently. This could cause discomfort in subcutaneous or external pacing arrangements.

The more gradual rising edge 106 contributes to reducing the pulse's higher-order harmonics (i.e., high-frequency spectral power density). This result is beneficial to reducing the degree of stimulation of nerve and skeletal muscles, which in turn reduces the discomfort felt by the patient, while delivering an effective quantity of charge over the duration of the pulse so as to achieve sufficient cardiac cell capture.

One drawback of using a slower rising edge is a loss of efficiency in the operation of the pulse generator. Whereas trans-cutaneous (i.e., external) pacing is generally performed by line-powered devices, or devices having large-capacity batteries or easily-replaceable batteries and therefore is less concerned with operational efficiency, implantable devices have limited size and battery capacity, and replacement of the device or battery requires performing a surgical procedure to reach the device. Thus, operational efficiency is a substantial concern for implantable devices. In limited slew rate embodiments, producing the slowly-rising edge 106 involves greater internal dissipation of energy in the IPG, and does relatively little in the patient while the rising amplitude remains below the capture threshold. Thus, in the present embodiment, an initially fast rising edge 102 is employed to advance the pulse amplitude to a level ideally below the activation threshold of pain receptors or non-targeted musculature of the patient. This pain or discomfort threshold can be determined individually for each patient after implantation of the device according to one embodiment. In another embodiment, as a more coarse rule-of-thumb, the point 104 where the slew rate is slowed is set between ¼ and ½ of the peak amplitude 108.

Figure 2B:
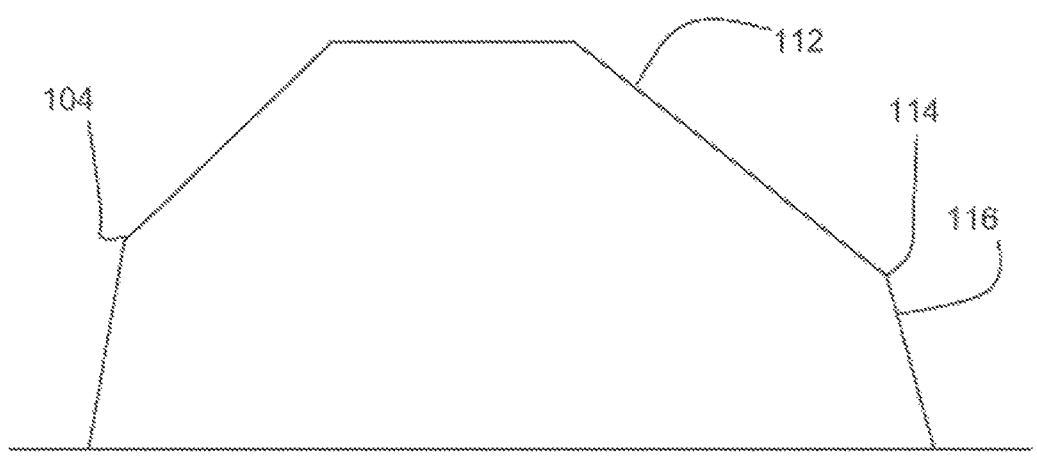

FIG. 2B illustrates a similar waveform according to another embodiment, in which the pulse is not truncated; rather, the peak is followed by a gradual falling edge 112 until point 114, after which a steep falling edge 116 concludes the pulse. In this approach, high-frequency components are further reduced with the more gradual transition on the trailing edges. Point 114 can be set to just below the threshold for stimulating pain receptors or activating non-targeted muscle cells, or it can be set to a nominal value relative to point 104 on the leading edge. As depicted, point 114 can be at a different level than leading edge transition point 104, taking into account any changes in the stimulation threshold as a result of the administration of the pulse.

Figure 2C:
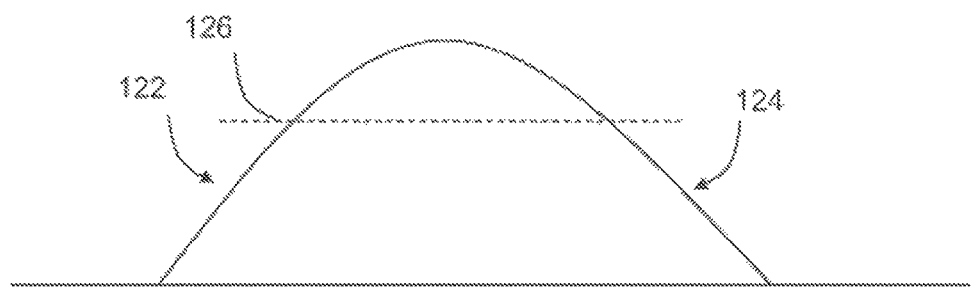

FIG. 2C illustrates a waveform according to another embodiment, in which the wave shape of the pulse is sinusoidal. As depicted, the pulse has the shape of a positive half-wave. Unlike the trapezoidal or modified-trapezoidal wave shape embodiments described above, this pulse has no flat, constant-amplitude portion. The rising and falling edges 122 and 124 respectively, are not distinctly defined in the overall wave shape, and they are not linear. This embodiment has the benefit of further reducing the spectral power distribution. A pure sine half-wave that begins and ends at zero amplitude has no discontinuities and thus minimal harmonics in its spectrum. The amplitude and fundamental frequency of the waveform is set such that the duration of the pulse which meets or exceeds the pacing threshold (i.e., having an amplitude greater than pacing threshold 126) is sufficiently long to ensure cardiac cell capture (e.g., 3-8 ms).

Figure 2D:
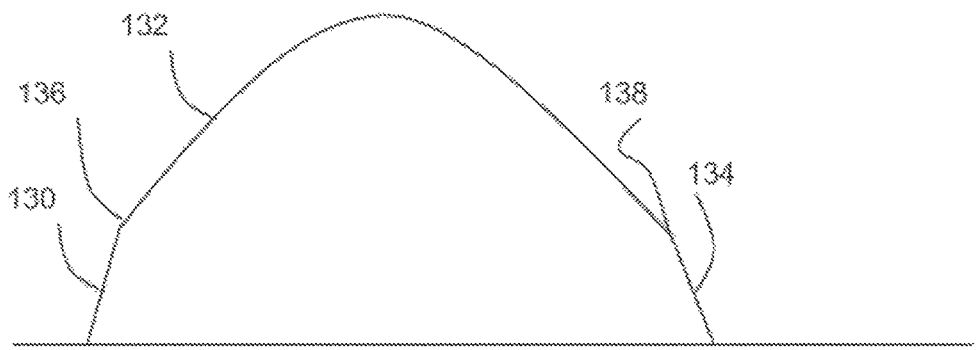

FIG. 2D illustrates a waveform according to a related embodiment that has a compound waveshape having an initially fast rise time 130, followed by a sinusoidal portion 132, which is in turn followed by a fast falling edge 134. The sinusoidal portion takes up a majority of the pulse duration. The transition points 136 and 138 are selected at amplitudes corresponding to the nerve or non-cardiac muscle stimulation thresholds. This waveform represents a trade-off between improved operating efficiency at the initial and final fast edges, and increased spectral content as a result of the non-differentiable current at the transition points 136 and 138.

Figure 3:
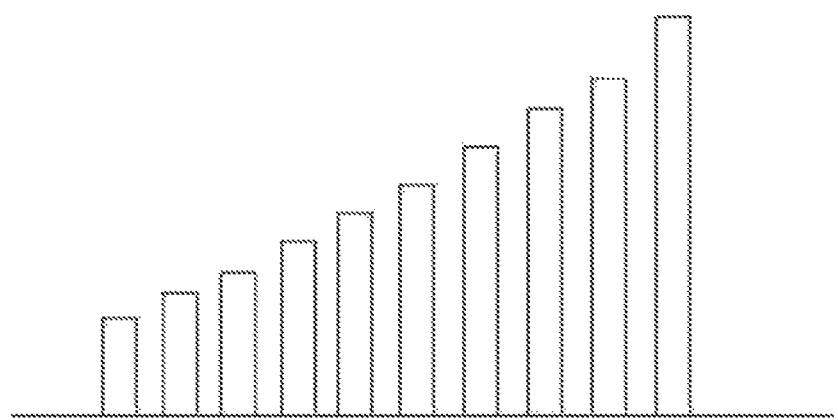
FIG. 3 is a waveform diagram illustrating a series of electrotherapy pulses with each successive pulse having a greater pulse amplitude than its preceding pulse according to one type of embodiment.

In a related embodiment, as depicted in FIG. 3, the pulse amplitude is ramped up across a series of pulses with each pulse having a peak amplitude higher than the preceding pulse. The step-wise pulse amplitude increases within a series of pulses can be halted when the device detects that cardiac cells have been successfully captured. Known techniques for detecting cardiac capture (e.g., impedance measurement across a region that includes the heart) can be employed to this end. The effective pulse amplitude for a treated arrhythmia episode can be stored on-board the IPG and used to calculate the initial amplitude at the beginning of the following arrhythmia episode. The pulses are shown in FIG. 3 as having basic square waveforms for the sake of simplicity. However, the principle of varying the amplitude of successive pulses is applicable to any waveform described herein, including the waveforms of FIGS. 2A-2D, as well as others not specifically described.

Figure 4:
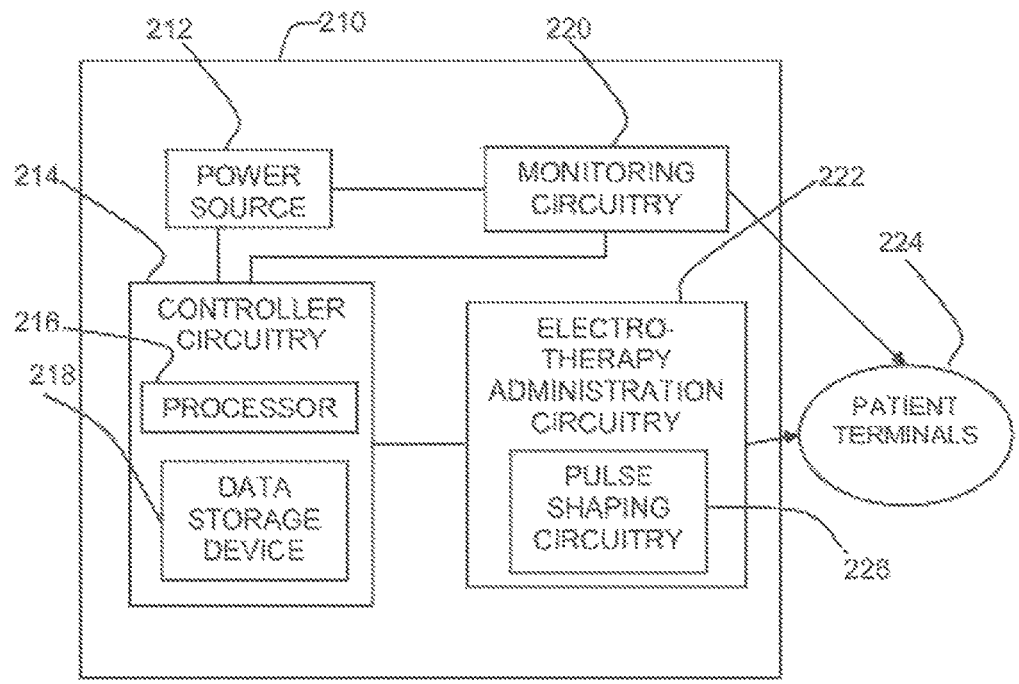
FIG. 4 is a block diagram illustrating a subcutaneous electrotherapy device according to aspects of the invention.

FIG. 4 is a block diagram illustrating an implantable pacing system 210 adapted for far-field pacing (without a transvenous lead) according to one embodiment. The electrotherapy administration circuitry 222 is electrically coupled to the patient terminals 224, which can be selectively connected to subcutaneously-implanted electrodes or to the housing of the device (i.e., the can). The electrotherapy administration circuitry 222 generates and delivers pulses having specified parameters. Electrotherapy administration circuitry 222 includes pulse shaping circuitry 226, which is constructed to adjust the parameters of the pulses, including the waveform, pulse width, pulse period, pulse amplitude and pulse slew rate in response to a control signal. The monitoring circuitry 220 is electrically coupled to the patient terminals 224 as well as the power source 212 and is constructed to monitor the patient for indicia of arrhythmia. The monitoring circuitry 220 can further include sensing circuitry to detect physiologic responses to the electrotherapy. Examples of such sensing circuitry include electromyography (EMG) sensing circuitry coupled to the patient terminals, an accelerometer positioned in the housing of the device, a minute ventilation sensing arrangement, impedance measurement circuitry, hemodynamic sensors or other cardiac rhythm management sensors known in the art. The physiologic responses can be indicators of effectiveness of the electrotherapy (e.g., cardiac cell capture), possible discomfort exhibited by the patient, or a combination thereof.

Power source 212 contains an on-board energy store sufficient to power the device and to generate the electrotherapy energy. Any suitable battery technology known in the art may be employed. The controller circuitry 214 is electrically coupled to the power source 212, monitoring circuitry 220 and the electrotherapy administration circuitry 226. The controller circuitry includes a processor circuit 216, associated interface circuitry (not shown), which can include analog-to-digital converting circuitry, digital-to-analog converting circuitry, address and data busses, communication circuitry to facilitate data input/output exchange with an external communicator, and a data storage device 218. The controller circuitry 214 stores program instructions that define all aspects of the operation of the device, including decision logic to administer electrotherapy, the electrotherapy waveforms and logic for selecting or adjusting the waveform parameters, logic for monitoring the patient and initiating, ceasing, or adjusting the electrotherapy in response, discomfort management control logic, and the like. These instructions are stored in data storage device 218, which is a non-transitory, machine-readable storage medium, such as a non-volatile memory device. Storage device 218 also stores the various electrotherapy parameters In operation, controller circuitry 214 can monitor the output from the monitoring circuitry 220 to determine when therapy is appropriate and to modify the parameters of the electrotherapy during an arrhythmia episode being treated. When preferred parameters such as waveform parameters, pulse delivery vector, etc., are established, these parameters can be stored in the data storage device 218 and accessed by the processor 216 to control the delivery of the electrotherapy via the electrotherapy administration circuitry 222.

The electrotherapy administration circuitry 222 can be adapted to produce artificial pacing pulses, each delivering sufficient charge through the patient terminals 224 to capture cardiac cells and initiate a cardiac cycle. The amount of charge necessary may vary based on the positioning of the patient terminals 224.

Figure 5:
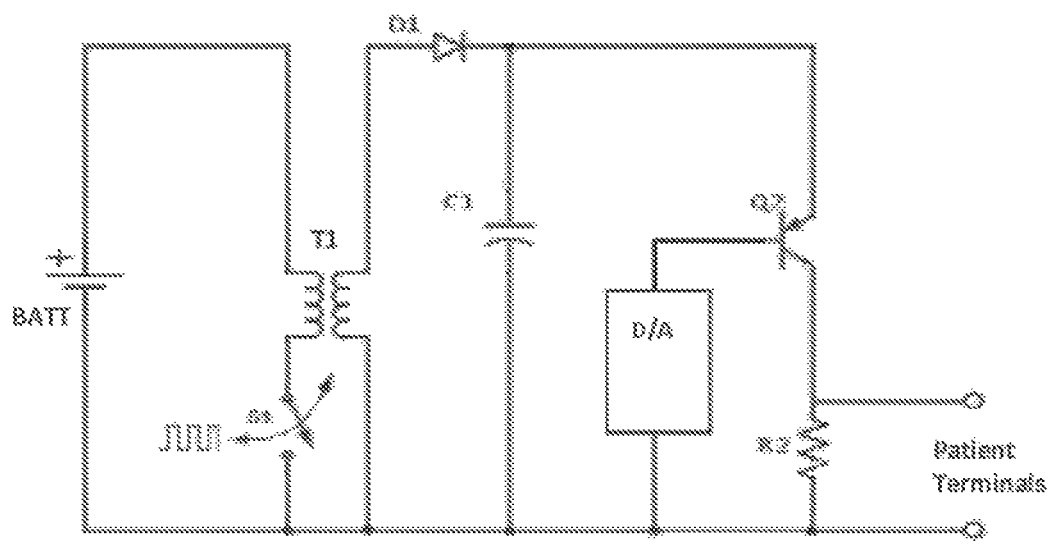
FIG. 5 is a diagram illustrating an example pulse shaping circuit according to one aspect of the invention.

FIG. 5 is a simplified circuit diagram of electrotherapy administration circuitry according to one example embodiment, which represents a circuit constructed to produce selected waveforms such as the ones described above with reference to FIGS. 2A-2D and FIG. 3. Switch S1 is cycled rapidly (and with variable duty cycle) to repetitively energize transformer T1, which is configured in a flyback converter arrangement to boost the voltage from the battery power source BATT. Transformer T has a primary-to-secondary winding ratio of n:m, with m being greater than n to increase the voltage on the secondary side. The winding ratio is also selected in accordance with the operating duty cycle, as per conventional flyback circuit design practices. The secondary side of T1 produces an output current through the rectifying diode D1, which charges capacitor C1. The voltage on capacitor C1 is thus maintained at the desired far-field pacing level of 10-60 volts, for example, and this voltage can be adjusted to some extent by the duty cycle control of switch S1, to which the control signal can be provided by the controller or an adjustable pulse-width modulation (PWM) circuit controlled by the controller. A digital-to-analog converter circuit D/A generates a signal corresponding to the desired waveshape and timing requirements for the waveform. The D/A circuit is interfaced with the controller, which ultimately selects and defines the waveform according to its program logic. The output of the D/A circuit is fed to output driver Q2 to deliver the pacing waveform to the patient terminals. In the simplified embodiment depicted, output driver is an inverting configuration, requiring the output of the D/A circuit to be inverted. Various other circuit topologies are contemplated according to related embodiments, with the possibility of using any suitable topology capable of providing the electrotherapy waveforms described herein, including, for instance, a push-pull amplifier output stage, a feedback controlled-amplifier circuit, etc.

One notable feature of this type of electrotherapy administration circuit is the use of an active load in the driver stage. This differs from certain conventional IPG circuits in that conventional circuits typically use fast switching to create square or steep trapezoidal waveshapes, or truncated exponential waveshapes produced by capacitive discharge. In this embodiment, the circuit drives the desired waveform like an electrical function generator. This advanced waveshaping technique facilitates variably-controlled rise and fall times of the leading and trailing edges of pulses, as well as compound waveforms with multiple, time-controlled, slew rates, and sinusoidal and other waveforms, which can be software-defined in the controller.

Figure 6:
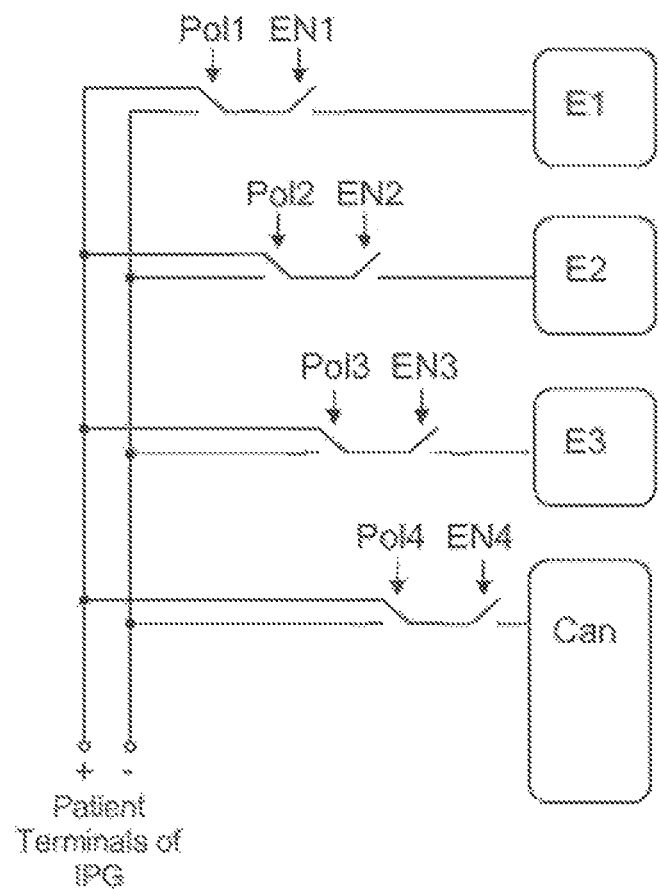
FIG. 6 is a diagram illustrating a switching arrangement for selecting an electrotherapy application vector according to one embodiment.

FIG. 6 illustrates an electrode selection arrangement for a subcutaneous device according to one embodiment. The patient terminals of the IPG are selectively connectable to each of a set of electrodes positioned at different locations in the patient. The metal housing of the IPG, i.e., the can, can itself serve as an electrode. In this exemplary switching arrangement, each electrode E1-E3 and the Can can be separately enabled or disabled according to a respective enable signal EN1-EN4. Also, each electrode can be selectively coupled to either the + or the − terminal of the patient terminals, facilitated by polarity selector switches POL1-POL4. This selection facilitates variation of the pulse polarity, as may be called for by the electrotherapy administration algorithm implemented in the controller. The various possible electrode and polarity combinations (including selecting individual or electrically-connected groups of electrodes to be the cathode and anode for a given electrotherapy application), are each an individual electrotherapy application vector. As will be described in greater detail below, one aspect of the invention is directed to adjusting the vector to mitigate patient discomfort.

In one embodiment, device 210 includes provisions for inferring discomfort in the patient evoked by application of the electrotherapy. According to one exemplary arrangement, monitoring circuitry 220 includes evoked response sensing circuitry that is constructed to sense indicia of discomfort response in the patient. One such indicator is movement in the patient. In an example embodiment, the evoked response sensing circuitry includes an accelerometer device. The controller circuitry 14 can be configured to infer evoked discomfort responses in the form of sudden motion sensed by the accelerometer that is temporally correlated with the application of electrotherapy. According to one algorithm for inferring evoked discomfort response, in a time window that begins immediately, or at a defined time delay measured from the start of each pulse, for example, if a sudden motion is detected and, optionally, if this motion appears over a defined number of pulses, a discomfort response is recognized by the controller.

In a related embodiment, EMG sensing using some or all of the subcutaneous electrodes available for electrotherapy application (e.g., electrodes not being used for the presentlyapplied vector, or even the same electrodes), or using separate electrodes from the electrotherapy-administering electrodes, is employed to sense signaling to the patient's musculature. In the EMG sensing, known techniques for filtering and other signal processing can be employed in the controller to obtain an EMG detection of suitable quality. In similar fashion to the time correlating determination exemplified above for movement sensing via accelerometer, the EMG sensing is detected in the monitoring window associated with each applied pulse, and an inference is made based on a period of observation over one or more pulses. This evoked discomfort response can be used to improve parameters for electrotherapy application.

The monitoring circuitry can also detect effectiveness of the electrotherapy. For instance, measurement of impedance across the heart can indicate whether a heartbeat was triggered by a pacing pulse. Various known sensing and detection techniques to measure effectiveness of electrotherapy can be utilized in different embodiments.

A related aspect of the invention involves inferring discomfort experienced by the patient during administration of electrotherapy and using that discomfort data to vary the parameters of administering the electrotherapy. The discomfort inference can be achieved via the evoked response sensing described above. The variation of parameters can include one or more of the following:
  waveform amplitude adjustment;
  basic waveshape selection (e.g., truncated, trapezoidal, sinusoidal, etc.);
  compound waveform selection;
  slew rate adjustment;
  compound slew rate selection;
  compound waveform/slew rate transition point adjustment;
  electrotherapy administration vector selection (including polarity selection).

A wide variety of adjustment algorithms are contemplated according to various embodiments. In one high-level example, discomfort response criteria manages selection or adjustment of electrotherapy parameters in the following order or precedence (from highest to lowest):
  (1) electrotherapy effectiveness (i.e., effective conversion of arrhythmia);
  (2) discomfort mitigation
  (3) operational efficiency.
Thus, in this example, of primary concern is treatment of the patient's arrhythmia. In a related embodiment, some level of discomfort (with defined limits) is acceptable based on a defined trade-off that can depend on the severity of the arrhythmia being experienced. For instance, a more severe tachycardia that, if untreated, can lead to a life-threatening condition, would call for more aggressive ATP treatment and a greater discomfort allowance. On the other hand, a less-severe arrhythmia would not require such aggressive treatment, and indeed, the order of precedence of (1) and (2) above may be reversed in those cases. There are numerous permutations of parameter variability contemplated. Notably, it is possible to have predefined a default ordering, and still further, in one embodiment, different orderings may be defined, with a particular ordering set being selected based on a historic result of parameter variation in the patient.

FIG. 7 is a flow diagram illustrating an exemplary process of optimizing the electrotherapy parameters while taking discomfort into account, which uses the primary order of precedence of (1)-(3) outlined above. At 302, electrotherapy effectiveness monitoring is used to determine if the treatment is effective (i.e., are pacing pulses achieving capture of the heart to initiate a heartbeat?). If not, a subroutine to increase the effectiveness is called at 308. In one embodiment, this subroutine first adjusts the application vector, then the waveform, then the pulse amplitude. Other orders of operation are contemplated in various related embodiments. In a related embodiment, successful and unsuccessful combinations of electrotherapy parameters are stored for future reference. These stored values may have an expiration date associated with them to account for changes over time that can render such results obsolete.

If the electrotherapy is effective, the optimization routine advances to decision 304 in which the evoked discomfort response inference is checked to infer if the patient is experiencing discomfort. If the patient is not discomfort-free, then a discomfort mitigation subroutine is called at 310 to vary electrotherapy parameters. In one exemplary subroutine, parameters associated with unsuccessful electrotherapy effectiveness, and less aggressive variations of those parameters, are excluded from the set of possible parameters to try. In one specific approach, the electrotherapy parameters are varied in the following order to address discomfort: vector, pulse amplitude, waveform. Successful and failed parameter adjustments relating to discomfort are stored (temporarily or otherwise) for future reference. To ensure efficacy, effectiveness is checked by looping back to decision 302.

With items (1) and (2) being taken care of, i.e., effective electrotherapy being applied and discomfort being managed, the process proceeds to decision 306 to explore opportunity to adjust parameters to reduce energy consumption (i.e., battery drain) and therefore increase operational efficiency and life of the implanted device. Accordingly, if the electrotherapy is not maximally efficient (i.e., at the lowest pulse amplitude and using the sharpest waveform), then a subroutine to increase efficiency is called at 312. This subroutine can avoid failed configuration parameter combinations from subroutines 308 and 310. In one embodiment, the parameters are varied in the following order: pulse amplitude, waveform, vector.

In one example of varying some of the parameters in response to the evoked discomfort response, a set of therapy delivery vectors best adapted to reduce discomfort is selected along with the pulse amplitude. The controller circuitry is configured to deliver a first therapeutic stimulation at an initial amplitude to vector A and observe an evoked response (cardiac capture), then to deliver a second stimulation using vector B and observe the evoked response in a similar way. This procedure can be followed until all vectors have been evaluated. The performance of each vector can be compared and the vector with the best performance is utilized for sensing, discomfort control or therapy. If one vector results in the desired treatment outcome, that vector is utilized and the device then seeks to reduce any discomfort (e.g., reducing the pulse amplitude by a defined step size such as 10%, for example) and monitors the cardiac response in terms of capture for ATP. If the desired therapeutic result is not achieved the amplitude can be increased for the last successful vector with the lowest effective amplitude. In this way the optimum vector can be found that uses the lowest amplitude resulting in the lowest possible discomfort induced by the therapeutic stimulus.

When the therapeutic result is not achieved the amplitude is increased to the last effective amplitude that is then used for the remaining therapy. These vectors may be tested before discharging the patient from the hospital and the lower discomfort vectors stored in the data storage device of the controller. These vectors may also be tested and stored during an arrhythmia episode or during patient follow-up sessions.

In a related embodiment, instead of, or in addition to, automated adjustment of waveform and vector based on inferred discomfort response, the patient's feedback can be taken into account. In one approach, the data storage device is configured to store a list of pre-qualified pacing vectors, waveforms, and their appropriate minimum amplitudes that have been approved for therapy in the specific patient by a physician as part of in-clinic threshold testing. Notably, different thresholds can be defined for anti-bradycardia and anti-tachycardia pacing. Also, a set of amplitudes, vectors, and waveforms can be separately defined for different tachycardia heart rates to particularly manage the ventricular effective refractory period (VERP) phenomenon in which the pacing threshold increases with increased tachycardia rates. Rather than using a high setting and low setting as known in conventional devices, determining patient-specific parameter settings can allow for better discomfort mitigation using all of the available variables provided by aspects of the present invention.

If the patient reports discomfort, then the patient or other clinical staff (such as a nurse or primary care physician) can then use a programming interface to vary the parameter vector for therapy from among the pre-qualified set of approved electrotherapy parameters. When a new vector is selected, the device will begin using that vector and the minimum amplitude determined by the physician.

In a related embodiment, the patient-based feedback can be used together with automated inferred evoked response-based adjustment. In one such approach, the automated adjustment is configured to make finer adjustments, whereas the patient-driven response can be used to make more dramatic changes to amplitudes and waveform parameters.

Figure 8A:
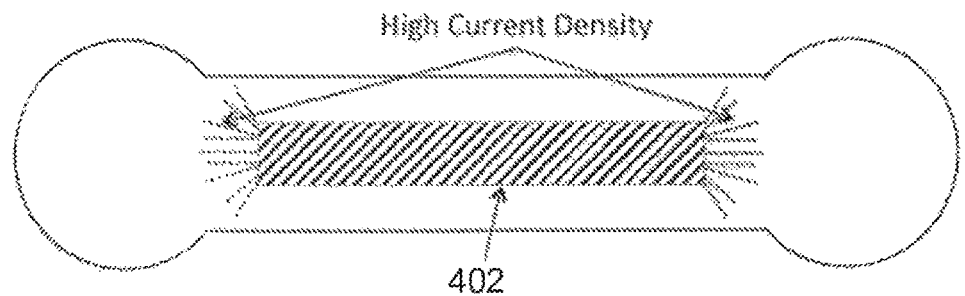
FIGS. 8A and 8B illustrate, respectively, a conventional subcutaneous electrode for use with an implantable pacemaker, and an improved lead having sensing electrodes that are utilized to reduce current density at the fringes of the primary electrode, according to one embodiment of the invention, which is beneficial for mitigating discomfort.
Figure 8B:
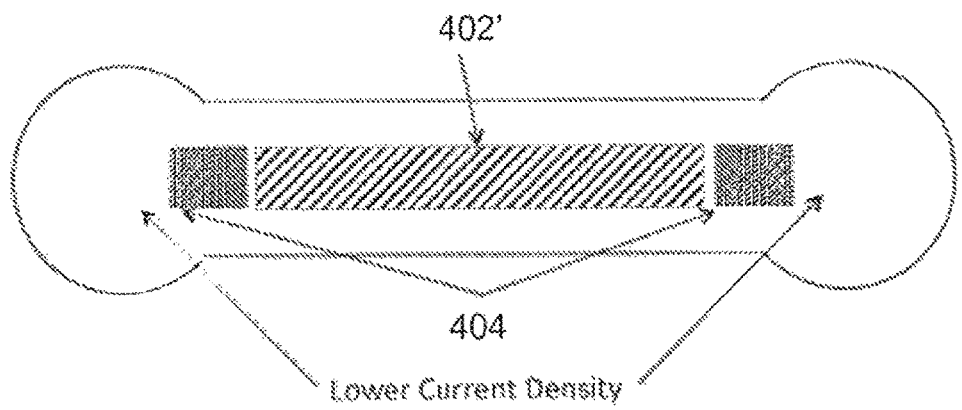

Another aspect of the invention relates to mitigating the discomfort experienced during therapy by reducing the edge effect of implanted leads in the body. FIG. 8A depicts an implantable lead for a subcutaneous system with a main stimulation coil 402. In this conventional system, the current density around the ends of the coil is very high during a stimulation pulse. This is because there is an abrupt fall-off in the potential at the ends. This "edge effect" causes increased nerve stimulation—and discomfort—since the higher current density captures more pain receptor neurons. In one embodiment of the invention, depicted in FIG. 8B, a reduced voltage is applied to two sensing electrodes 404 at each end of the coil in order to taper off the voltage and reduce the current density. Preferably, this reduced voltage would be 40-60% of the voltage on the main stimulation coil 402'.

The embodiments above are intended to be illustrative and not limiting. Additional embodiments are within the claims. In addition, although aspects of the present invention have been described with reference to particular embodiments, those skilled in the art will recognize that changes can be made in form and detail without departing from the scope of the invention, as defined by the claims.

Persons of ordinary skill in the relevant arts will recognize that the invention may comprise fewer features than illustrated in any individual embodiment described above. The embodiments described herein are not meant to be an exhaustive presentation of the ways in which the various features of the invention may be combined. Accordingly, the embodiments are not mutually exclusive combinations of features; rather, the invention may comprise a combination of different individual features selected from different individual embodiments, as will be understood by persons of ordinary skill in the art.

Any incorporation by reference of documents above is limited such that no subject matter is incorporated that is contrary to the explicit disclosure herein. Any incorporation by reference of documents above is further limited such that no claims that are included in the documents are incorporated by reference into the claims of the present Application. The claims of any of the documents are, however, incorporated as part of the disclosure herein, unless specifically excluded. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. An electrotherapy apparatus adapted for subcutaneous implantation for applying far-field pacing therapy for treating a patient experiencing an arrhythmia, the apparatus comprising:
a power source adapted to supply energy for operation of the apparatus;
a set of sensing electrodes, subcutaneously positionable in far-field relation relative to a heart of the patient, the sensing electrodes including a sensing electrode located at each end of a main stimulation coil configured to to create an edge effect that tapers a voltage present on the main stimulation coil, thereby reducing a current density in a vicinity of the edge effect;
electrotherapy administration circuitry electrically coupled to the power source and to a set of patient terminals, and constructed to generate electrotherapy pulses using the energy from the power source and apply a series of the electrotherapy pulses via the patient terminals in response to a control signal, the electrotherapy pulses being far-field pacing pulses, each delivering sufficient charge, through the set of sensing electrodes, to initiate a cardiac cycle;
monitoring circuitry electrically coupled with the power source and the set of patient terminals, and constructed to monitor the patient for indicia of the arrhythmia; and
controller circuitry electrically coupled with the power source, the electrotherapy administration circuitry, and the monitoring circuitry, the controller circuitry including a processor and a data storage device containing instructions that, when executed by the processor, cause the controller circuitry to read an output of the monitoring circuitry and determine any presence of the arrhythmia based on that output, and to generate the control signal causing the electrotherapy administration circuitry to apply the series of electrotherapy pulses.

2. The electrotherapy apparatus of claim 1, wherein the sensing electrode located at each end of the main stimulation coil tapers off voltage to a reduced voltage of forty to sixty percent of the voltage on the main stimulation coil.

3. The electrotherapy apparatus of claim 1, wherein current density is reduced at the fringes of a primary electrode where the main stimulation coil is present.

4. The electrotherapy apparatus of claim 1, wherein the electrotherapy administration circuitry includes a pulse shaping circuit.

5. An electrotherapy apparatus adapted for subcutaneous implantation for applying far-field pacing therapy for treating a patient experiencing an arrhythmia, the apparatus comprising:
- a power source adapted to supply energy for operation of the apparatus;
- electrotherapy administration circuitry electrically coupled to the power source and to a set of patient terminals, and constructed to generate electrotherapy pulses using the energy from the power source and apply a series of the electrotherapy pulses via the patient terminals in response to a control signal, the electrotherapy pulses being far-field pacing pulses, each delivering sufficient charge, through a set of sensing electrodes positioned subcutaneously in far-field relation relative to a heart of the patient, to initiate a cardiac cycle, the sensing electrodes including a sensing electrode located at each end of a main stimulation coil configured to create an edge effect that tapers a voltage present on the main stimulation coil, thereby reducing a current density in a vicinity of the edge effect;
- monitoring circuitry electrically coupled with the power source and the set of patient terminals, and constructed to monitor the patient for indicia of the arrhythmia;
- controller circuitry electrically coupled with the power source, the electrotherapy administration circuitry, and the monitoring circuitry, the controller circuitry including a processor and a data storage device containing instructions that, when executed by the processor, cause the controller circuitry to read an output of the monitoring circuitry and determine any presence of the arrhythmia based on that output, and to generate the control signal causing the electrotherapy administration circuitry to apply the series of electrotherapy pulses; and
- evoked response sensing circuitry electrically coupled to the controller circuitry, the evoked response sensing circuitry being constructed to sense indicia of movement by the patient, and the controller circuitry being further configured to infer whether the movement is an evoked response to the administration of the electrotherapy pulses, and to adjust application of subsequent electrotherapy pulses in response to an inference of the evoked discomfort response.

6. The electrotherapy apparatus of claim 5, wherein the evoked response sensing circuitry includes an accelerometer.

7. A method for treating an arrhythmia in a patient using an electrotherapy device, the method comprising:
- monitoring, by the electrotherapy device, the patient for indicia of the arrhythmia;
- determining, by the electrotherapy device, the presence of the arrhythmia based on the indicia; and
- applying to the patient, by the electrotherapy device, a series of electrotherapy pulses in response to the presence of the arrhythmia through a set of sensing electrodes positioned subcutaneously in far-field relation relative to a heart of the patient to initiate a cardiac cycle, the sensing electrodes including a sensing electrode located at each end of a main stimulation coil providing and configured to substantially embody the end of the main stimulation coil to create an edge effect that tapers a voltage present on the main stimulation coil, thereby reducing a current density in a vicinity of the edge effect.

8. The method of claim 7, wherein the sensing electrode located at each end of the main stimulation coil tapers off voltage to a reduced voltage of forty to sixty percent of the voltage on the main stimulation coil.

9. The method of claim 7, wherein current density is reduced at the fringes of a primary electrode where the main stimulation coil is present.

10. The method of claim 7, wherein the series of electrotherapy pulses are generated by an electrotherapy administration circuitry including a pulse shaping circuit.

11. The method of claim 7, further comprising:
- sensing indicia of discomfort response in the patient;
- detecting evoked discomfort response resulting from administrating of the electrotherapy pulses; and
- adjusting application of subsequent electrotherapy pulses in response to a detection of the evoked discomfort response.

12. The method of claim 11, further comprising:
- detecting the evoked discomfort response based on sudden motion sensed by the electrotherapy device correlated with application of the electrotherapy.

13. The method of claim 11, further comprising:
- varying a waveform parameter of the electrotherapy pulses in response to the detection of the evoked discomfort response.

* * * * *